US011830613B2

(12) United States Patent
Walker et al.

(10) Patent No.: US 11,830,613 B2
(45) Date of Patent: Nov. 28, 2023

(54) INTEGRATION OF A POINT-OF-CARE BLOOD ANALYZER INTO A PREHOSPITAL TELEMEDICINE SYSTEM

(71) Applicant: Physio-Control, Inc., Redmond, WA (US)

(72) Inventors: Robert G. Walker, Seattle, WA (US); Tyson G. Taylor, Bothell, WA (US); Alexander Esibov, Seattle, WA (US); Mitchell A. Smith, Sammamish, WA (US)

(73) Assignee: Physio-Control, Inc., Redmond, WA (US)

( * ) Notice: Subject to any disclaimer, the term of this patent is extended or adjusted under 35 U.S.C. 154(b) by 210 days.

(21) Appl. No.: 17/201,420

(22) Filed: Mar. 15, 2021

(65) Prior Publication Data

US 2021/0202083 A1 Jul. 1, 2021

Related U.S. Application Data

(63) Continuation of application No. 15/364,176, filed on Nov. 29, 2016, now Pat. No. 10,950,341.

(Continued)

(51) Int. Cl.
*G16H 40/63* (2018.01)
*G16H 10/60* (2018.01)
(Continued)

(52) U.S. Cl.
CPC ............. *G16H 40/63* (2018.01); *A61B 5/201* (2013.01); *A61B 5/7275* (2013.01);
(Continued)

(58) Field of Classification Search
CPC ............. G16H 40/60–67; G16H 80/00; G01N 33/48–98
See application file for complete search history.

(56) References Cited

U.S. PATENT DOCUMENTS 8,265,955 B2  9/2012  Michelson et al.
9,314,159 B2  4/2016  Lyon et al.
(Continued)

FOREIGN PATENT DOCUMENTS

WO  WO-03043494 A1 *  5/2003  ........... A61B 5/0002
WO  2016/077805 A2    5/2016

OTHER PUBLICATIONS

Kyriacou et al., Multi-purpose Healthcare Telemedicine Systems with mobile communication link support, Mar. 24, 2003, BioMedical Engineering OnLine (Year: 2003).*

(Continued)

*Primary Examiner* — Karen A Hranek
(74) *Attorney, Agent, or Firm* — McDonnell Boehnen Hulbert & Berghoff LLP

(57) ABSTRACT

A prehospital telemedicine system comprises a physiologic monitor; an electronic patient care reporting system (ePCR) system; and a point-of-care blood analyzer communicatively coupled to the physiologic monitor and the ePCR system. The point-of-care blood analyzer is configured to perform an analysis of a blood sample based on an indication of a need for a specific blood analysis provided by one of the physiologic monitor and the ePCR system, and to automatically transmit a result of the analysis to a remote data receiving system. The indication of a need for a specific blood analysis may be based upon any one of the following: vital signs data obtained for a patient by the physiologic monitor; and/or current documentation or past medical history captured on or available through the ePCR system.

19 Claims, 3 Drawing Sheets

Related U.S. Application Data

(60) Provisional application No. 62/261,258, filed on Nov. 30, 2015, provisional application No. 62/261,039, filed on Nov. 30, 2015, provisional application No. 62/261,050, filed on Nov. 30, 2015.

(51) Int. Cl.

| | | |
|---|---|---|
| *G16H 40/67* | (2018.01) | |
| *G16H 10/40* | (2018.01) | |
| *G16H 80/00* | (2018.01) | |
| *A61N 1/39* | (2006.01) | |
| *G16H 50/20* | (2018.01) | |
| *A61B 5/00* | (2006.01) | |
| *A61B 5/20* | (2006.01) | |
| *G16H 50/30* | (2018.01) | |
| *A61B 5/145* | (2006.01) | |

(52) U.S. Cl.
CPC ........... *A61N 1/3925* (2013.01); *G16H 10/40* (2018.01); *G16H 10/60* (2018.01); *G16H 40/67* (2018.01); *G16H 50/20* (2018.01); *G16H 80/00* (2018.01); *A61B 5/14546* (2013.01); *G16H 50/30* (2018.01)

(56) References Cited

U.S. PATENT DOCUMENTS

| | | | |
|---|---|---|---|
| 9,364,682 B2 | 6/2016 | Peterson et al. | |
| 2002/0115916 A1* | 8/2002 | Sjoqvist | A61B 5/0022 |
| | | | 128/903 |
| 2002/0196141 A1 | 12/2002 | Boone et al. | |
| 2003/0073931 A1 | 4/2003 | Boecker et al. | |
| 2004/0044546 A1* | 3/2004 | Moore | G16H 50/20 |
| | | | 705/2 |
| 2007/0282251 A1* | 12/2007 | Barvais | A61M 5/142 |
| | | | 604/67 |
| 2008/0065420 A1 | 3/2008 | Tirinato et al. | |
| 2008/0228094 A1 | 9/2008 | Audet et al. | |
| 2009/0222539 A1 | 9/2009 | Lewis et al. | |
| 2009/0234228 A1* | 9/2009 | Pintel | A61B 8/42 |
| | | | 600/443 |
| 2010/0152544 A1 | 6/2010 | Weaver et al. | |
| 2010/0218132 A1* | 8/2010 | Soni | G06F 16/21 |
| | | | 709/219 |
| 2010/0256990 A1 | 10/2010 | Horiguchi et al. | |
| 2011/0015938 A1* | 1/2011 | Rabinowitz | G06Q 10/00 |
| | | | 715/764 |
| 2011/0178373 A1* | 7/2011 | Pacey | G16H 40/63 |
| | | | 600/300 |
| 2012/0202705 A1 | 8/2012 | Oberbauer et al. | |
| 2012/0232367 A1 | 9/2012 | Allegri et al. | |
| 2013/0085778 A1 | 4/2013 | Guertin et al. | |
| 2013/0096649 A1* | 4/2013 | Martin | G16H 10/60 |
| | | | 607/60 |
| 2013/0331664 A1* | 12/2013 | Gilad-Gilor | A61B 5/741 |
| | | | 600/407 |
| 2014/0304638 A1* | 10/2014 | Yoshikawa | A61C 19/00 |
| | | | 715/771 |
| 2014/0365243 A1 | 12/2014 | Varadan et al. | |
| 2015/0142466 A1* | 5/2015 | Macoviak | G16H 40/67 |
| | | | 705/2 |
| 2015/0154367 A1 | 6/2015 | Shetty et al. | |
| 2015/0272689 A1 | 10/2015 | Shin et al. | |
| 2015/0331946 A1 | 11/2015 | Balwani | |
| 2016/0018963 A1 | 1/2016 | Robbins et al. | |
| 2016/0161510 A1 | 6/2016 | Görlinger | |
| 2016/0321414 A1* | 11/2016 | Salganicoff | G06N 20/00 |
| 2016/0328525 A1 | 11/2016 | Gross et al. | |
| 2017/0154160 A1 | 6/2017 | Walker et al. | |

OTHER PUBLICATIONS

Chen et al., Wireless local area network in a prehospital environment, Aug. 31, 2004, BMC Medical Informatics and Decision Making (Year: 2004).*

Thelen et al., A Multifunctional Telemedicine System for Prehospital Emergency Medical Services, 2013, Proceedings of the 5th International Conference on eHealth, Telemedicine, and Social Medicine (eTELEMED) (Year: 2013).*

Almadani et al., E-AMBULANCE: Real-Time Integration Platform for Heterogeneous Medical Telemetry System, Sep. 2015, The 5th International Conference on Current and Future Trends of Information and Communicaiton Technologies in Healthcare (ICTH 2015) (Year: 2015).*

Kost, Preventing Medical Errors in Point-of-Care Testing, Oct. 2001, Arch Pathol Lab Med, vol. 125 (Year: 2001).*

Mehran et al., A Simple Risk Score for Prediction of Contrast-Induced Nephropathy After Percutaneous Coronary Intervention, Oct. 6, 2004, Journal of the American College of Cardiology, vol. 44, Nol. 7, pp. 1393-1399 (Year: 2004).

F. H. Wians, Clinical Laboratory Tests: Which, Why, and What Do The Results Mean?, Feb. 1, 2009, Laboratory Medicine, vol. 40 No. 2, pp. 105-113 (Year: 2009).

Aging & Health A to Z: Heart Failure, Aug. 18, 2012, HealthinAging. com (Year: 2012).

Non-Final Office Action for U.S. Appl. No. 15/364,176 dated Dec. 17, 2018.

Final Office Action for U.S. Appl. No. 15/364,176 dated Jun. 10, 2019.

Advisory Action for U.S. Appl. No. 15/364,176 dated Aug. 14, 2019.

Non-Final Office Action for U.S. Appl. No. 15/364,176 dated Oct. 15, 2019.

Final Office Action for U.S. Appl. No. 15/364,176 dated Jan. 29, 2020.

Advisory Action for U.S. Appl. No. 15/364,176 dated Jun. 17, 2020.
Notice of Allowance for U.S. Appl. No. 15/364,176 dated Nov. 20, 2020.

Supplemental Notice of Allowance for U.S. Appl. No. 15/364,176 dated Feb. 16, 2021.

* cited by examiner

INTEGRATION OF A POINT-OF-CARE BLOOD ANALYZER INTO A PREHOSPITAL TELEMEDICINE SYSTEM

CROSS REFERENCE

This disclosure is a continuation of, and claims priority to, U.S. patent application Ser. No. 15/364,176 filed Nov. 29, 2016, which claims priority to the following U.S. provisional applications: U.S. Provisional Application No. 62/261,258, filed Nov. 30, 2015, titled "Integration of a Point-Of-Care Blood Analyzer into a Prehospital Telemedicine System"; U.S. Provisional Application No. 62/261,039, filed Nov. 30, 2015, titled "Increased Biomarker Measurement Accuracy through Multiplexing"; and U.S. Provisional Application No. 62/261,050, filed Nov. 30, 2015, titled "Multiplexing Strategies in a Point-of-Care Blood Testing Platform to Increase Diagnostic Utility of Test Results". Each of these applications is hereby incorporated by reference in its entirety.

TECHNICAL FIELD

The present disclosure relates generally, but not exclusively, to the field of telemedicine, and more particularly to a prehospital telemedicine and local area network for an emergency monitor-defibrillator system including a point-of-care blood analyzer.

BACKGROUND

For patients experiencing a medical emergency, blood analysis is often performed as a part of the diagnostic process. Various measurements may be made from a sample of a patient's blood, such as measurements of aspects of blood chemistry, or measurements of concentrations of biomarkers in the blood. Such an analysis is traditionally performed in a laboratory of a hospital, pursuant to a doctor's order. In these situations, the blood analysis results are sent to the doctor that ordered the test. For a patient with a pre-hospital emergency who is first contacted and treated by emergency medical services (EMS) and then transported to the hospital, a potential inefficiency in this process is that the blood analysis cannot be performed until the patient arrives at the hospital, and the hospital doctor may then have to delay medical decision-making and treatment until the blood analysis results become available. So-called Point-of-Care (POC) blood analysis systems have been developed, which can be used at the patient's side either inside or outside of the hospital, and which can shorten the time interval until an analysis result is available. However, such POC blood analysis systems have several potential limitations, particularly when considered for use in the prehospital environment. POC blood analysis systems frequently exhibit lower accuracy than blood analysis systems used in the central testing laboratory of a hospital. The decision of when it is appropriate to perform a certain test in the prehospital environment may be made by an EMS provider such as a paramedic with less training and experience than a doctor, and that provider must then manually interpret the results, manually enter test information into the medical documentation, and manually communicate the results to remote personnel or remote medical facilities. Accordingly, a goal of the present invention is to provide a system to enable blood testing to be performed safely and effectively, and to be integrated into other electronic data present within and shared between other medical devices in the patient's vicinity outside of a hospital setting, for example, in an emergency medical situation being attended to by a paramedic in an ambulance.

SUMMARY

The present disclosure concerns the integration of a portable blood analyzer into a point-of-care medical system remote from a hospital setting. More particularly, the present disclosure concerns a local area network for an emergency monitor-defibrillator system which incorporates a point-of-care blood analyzer, and which may be carried in an ambulance for use by a prehospital medical provider such as a paramedic. The point-of-care blood analyzer is communicatively connected in a local area network to other devices used by the paramedic, including a physiologic monitor in the form of, e.g., a monitor-defibrillator, and an electronic patient care reporting system embodied in, e.g., a tablet computer. (The term "paramedic", as used herein, is a shorthand for any pertinent prehospital provider, including but not limited to an emergency medical technician (EMT), nurse, or doctor.) The local area network of the monitor-defibrillator may additionally be connected to remote personnel, medical facilities, and data systems for purposes of remote monitoring and telemedicine. A system such as this enables numerous efficiencies and advantages to enhance the medical system performance and the quality of patient care. For example, such a system enables a required blood analysis to be performed in the prehospital environment when EMS begins caring for the patient, and enables results of the analysis to be automatically and instantly communicated to the hospital, before the patient reaches the hospital, which in turn enables the hospital to be better prepared to treat the patient in a timely fashion. The results of the analysis can be automatically combined with other patient or diagnostic information to provide greater insight than the results of the blood test alone, and can be automatically and accurately documented in appropriate medical records, checklists, or decision tools. Appropriate selection of patients for diagnostic testing is a recognized problem throughout medicine, and may be of proportionally greater concern in the prehospital emergency care environment where providers often have less training and experience than medical doctors, and are often under greater time pressure and stress. Accordingly, a more intelligent system would allow enforcement of rules to restrict paramedics and other emergency medical personnel from performing blood tests until certain criteria (such as application of a clinical decision rule, the presence of specific physiologic monitoring values, or the presence of specific patient demographics or physical assessment details) are met, allowing EMS agencies to more confidently introduce prehospital blood tests for which judicious patient selection is important. In an illustrative embodiment of the invention, a prehospital local area network for an emergency monitor-defibrillator system comprises a physiologic monitor; an electronic patient care reporting system (ePCR) system; and a point-of-care blood analyzer communicatively coupled to the physiologic monitor and the ePCR system. The point-of-care blood analyzer is configured to perform an analysis of a blood sample based on an indication of a need for a specific blood analysis provided by one of the physiologic monitor and the ePCR system, or alternately based on the discretion of the prehospital provider, and to automatically transmit a result of the analysis to a remote data receiving system through a telemedicine component of the local area network. In the illustrative embodiment, the indication of a need for a specific blood analysis may be based upon any one or more of the following: vital signs data obtained for a patient by the physiologic monitor; current documentation captured on the ePCR system; past medical history accessed from a remote medical record via a telemedicine component of the local area network; a care process checklist or prompted protocol electronically displayed on the monitor-defibrillator or the ePCR system. Moreover, the point-of-care blood analyzer may be further configured to perform the analysis based on a user's independent decision to initiate a blood analysis.

In the illustrative embodiment, the remote data receiving system can be configured to automatically activate at least one of an alert, a resource mobilization, or a care protocol upon receiving the result of the blood analysis. (Examples of a "resource mobilization" include, but are not restricted to, activation of a catheterization laboratory, preparation and delivery of blood products from a blood bank, preparation and retrieval of a medication from a pharmacy, and prioritization for use of an imaging resource, such as a CT scanner. A "care protocol" is a written plan for medical treatment.) Alternatively, or in addition, the point-of-care blood analyzer can be further configured to automatically inform the remote data receiving system that a blood analysis is in progress, what analysis result will be forthcoming, and to initiate a countdown timer at the remote data receiving system indicating the wait time until the analysis result will be available. The analysis result can be automatically transmitted to the remote data receiving system following a preconfigured data routing path, which may have previously been used to transmit a prior diagnostic test result, e.g., an electrocardiograph (ECG). In a more specific embodiment, a 12-lead ECG indicative of ST-Elevation Myocardial Infarction (STEMI) is transmitted to the remote data receiving system located at a hospital and configured to alert the hospital to begin mobilizing resources—e.g. activating the cardiac catheterization lab—and preparing for expeditious care of the patient. In this embodiment, the point-of-care blood analyzer can be further configured to perform a blood test to assess the patient's kidney function (for example, via measurement of the serum creatinine level) and automatically transmit a result of the blood test to the remote data receiving system, thus additionally alerting the hospital to the patient's risk for contrast-induced nephropathy, avoiding the need to wait on the results of kidney function tests once the patient arrives at the hospital, and allowing more time for the hospital and prehospital providers to take measures that may mitigate the patient's likelihood of developing contrast-induced nephropathy.

In an alternative or further embodiment, the prehospital telemedicine system comprises a point-of-care blood analyzer communicatively coupled to at least one of a physiologic monitor and an ePCR system. The blood analysis is contingent upon completion of an electronic checklist or clinical decision rule, which may be implemented on the ePCR system or physiologic monitor. (It should be noted that gating the blood test based on a checklist or clinical decision rule may be done regardless of whether or not the prehospital system is communicatively coupled to a remote data receiving system.) Once the checklist or decision rule has been completed, and the result indicates that it is appropriate to perform the blood analysis, then the ePCR or physiologic monitor electronically enables the point-of-care blood analyzer to perform the analysis. The information used to complete the electronic checklist or clinical decision rule includes any combination of: information entered by a user on the physiologic monitor or ePCR, physiologic monitoring information automatically obtained from the physiologic monitor, and information automatically obtained from the ePCR. The information used for the electronic checklist or clinical decision rule could also include information from an electronic medical record, that might be remotely located, such as in a hospital-based electronic medical records system. Other combinations and permutations of these features will be evident to one skilled in the art.

The present invention also encompasses a method of using a prehospital telemedicine system to improve treatment of a patient undergoing a medical emergency. In an illustrative embodiment, the inventive method comprises communicatively coupling a point-of-care blood analyzer with at least one of a physiologic monitor and an ePCR system, and then using the point-of-care blood analyzer to perform an analysis of a blood sample based on an indication of a need for a specific blood analysis provided by one of the physiologic monitor and the ePCR system. Additional features of the inventive system and method are described below.

DETAILED DESCRIPTION OF ILLUSTRATIVE EMBODIMENTS

As discussed above, a primary aspect of the present disclosure concerns the integration of a point-of-care blood analyzer into a prehospital telemedicine system. For example, the point-of-care blood analyzer may be networked into a local area network (LAN) for an emergency monitor-defibrillator that may optionally also incorporate a telemedicine system connecting the monitor-defibrillator to remote individuals, medical facilities, and/or data repositories. Other aspects of the present disclosure include increased biomarker measurement accuracy through multiplexing, and multiplexing strategies in a point-of-care blood testing platform. Each of these is described below.

Integration of a Point-of-Care Blood Analyzer into a Local Area Network for an Emergency Monitor-Defibrillator and an Associated Prehospital Telemedicine System The present specification describes various embodiments of integration of a point-of-care blood analyzer into a local area network for an emergency monitor-defibrillator and an associated prehospital telemedicine system to accomplish certain efficiencies and advantages related to use of the blood analyzer in the prehospital environment. For purposes of the present disclosure, the term "telemedicine system" is intended to connote a real-time, unidirectional or bidirectional data connection between the monitor-defibrillator local area network and one or more remote locations. Although such a real-time data connection is employed in illustrative embodiments, the scope of protection of the claims at the end of this specification is intended to encompass situations in which the invention is employed strictly within the local area network of the monitor-defibrillator, without the requirement of a real-time data connection to a remote location, unless the claims specifically require such a real-time data linkage.

Figure 1:
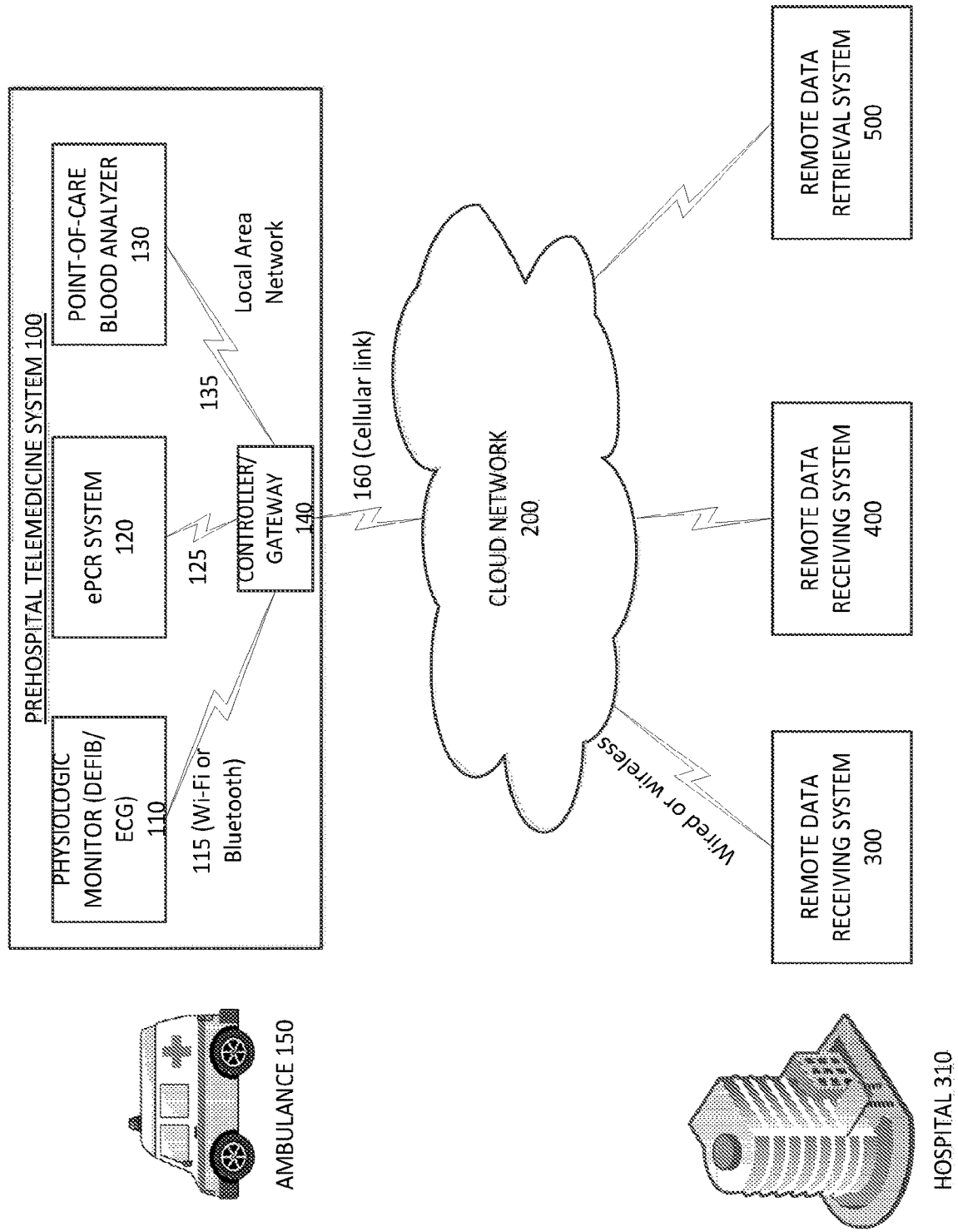
FIG. 1 schematically depicts an illustrative embodiment of the present invention in which a prehospital telemedicine system is communicatively coupled to one or more remote data receiving systems through a cloud network.

Referring to FIG. 1, the inventive prehospital monitor-defibrillator local area network 100 comprises a physiologic monitor 110, an electronic patient care reporting system (ePCR), and a point-of-care blood analyzer 130. (Note that the prehospital monitor-defibrillator local area network 100 is sometimes referred to simply as the prehospital system 100.) The components of the local area network, including the blood analyzer, may be communicatively coupled directly to each other, or may be coupled via a central controller/gateway 140 as illustrated in FIG. 1. The point-of-care blood analyzer 130 is configured to perform an analysis of a blood sample based on an indication of a need for a specific blood analysis provided by one of the physiologic monitor 110 and the ePCR system 120, and to automatically transmit results of the analysis to a remote data receiving system via a telemedicine component. In cases where the prehospital system 100 is carried by an ambulance 150, or other emergency services vehicle, the system includes a gateway device 140, which may also serve as a controller for the system 100. The gateway device 140 is configured to wirelessly communicate (for example, using Wi-Fi or Bluetooth, or any other suitable wireless communication protocol) with the physiologic monitor 110, ePCR system 120, and point-of-care blood analyzer 130. (The point-of-care blood analyzer could alternatively be configured to only communicate with the physiologic monitor or the ePCR, and not have a direct link to the gateway. Also, the gateway could alternatively be a part of the physiologic monitor or the ePCR device, rather than a separate component of the system.) Such wireless communications are represented in FIG. 1 by wireless links 115, 125, and 135, respectively. Moreover, the gateway device 140 may include a cellular transceiver to communicate over a cellular link 160 to a cloud network 200. The cloud network 200 in turn communicates (using available wireless or wired data communications links) with one or more remote data receiving or retrieval systems 300, 400, 500, etc. For example a remote data receiving system 300 may be located at a hospital 310, as shown. Moreover, "retrieval" refers to accessing information from a remote patient medical record, or any other information flowing back to the prehospital provider. Accordingly, remote system 500 is indicated in FIG. 1 to be a remote data retrieval system, although any of the remote systems could also be configured to retrieve information and to send some or all of the retrieved information back to the prehospital system 100.

Although the predominant use of the telemedicine component providing a link to remote locations is for unidirectional transmission of data from the prehospital monitor to a receiving hospital, it should be noted that in some cases it may be appropriate to have bidirectional data flow, e.g., information could be pulled from a remote medical record back to the prehospital system, to variously help determine appropriateness of performing a test, or combine with analysis results to produce a derived score or index, etc., which may then be transmitted back through the telemedicine link to a receiving hospital or physician. Such variations should be apparent to those skilled in the art.

Figure 2:
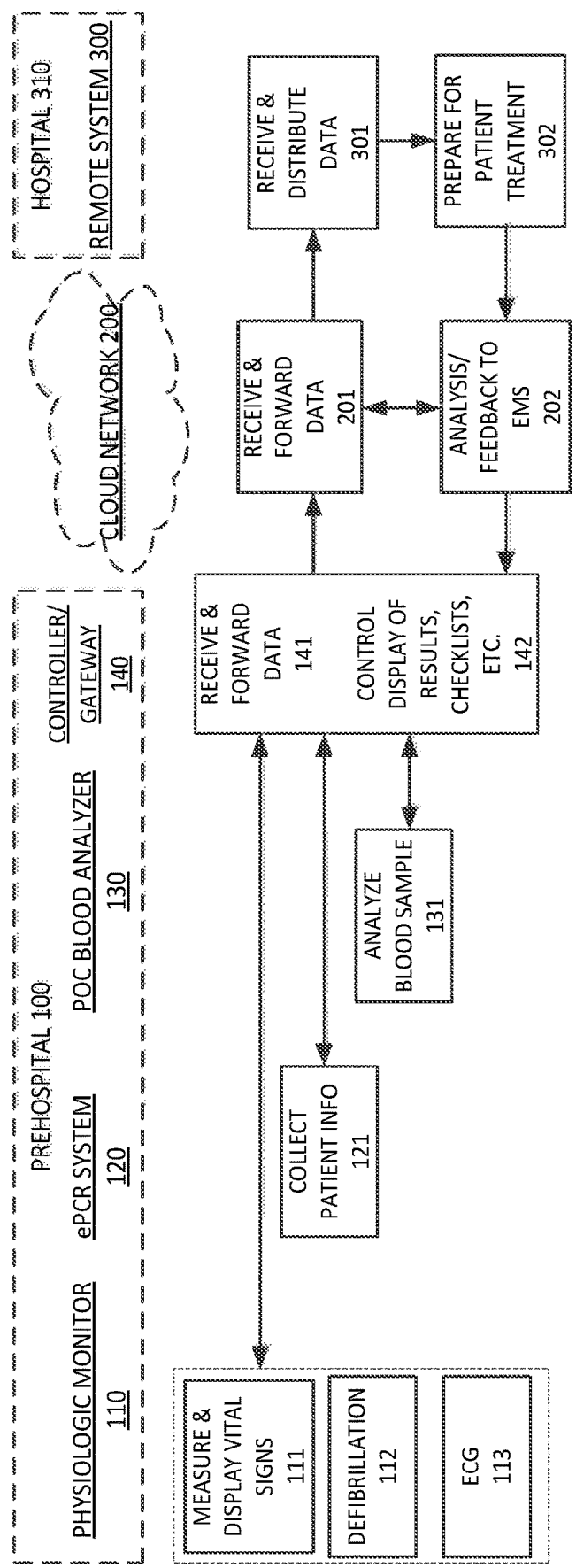
FIG. 2 is a diagram illustrating operations of, and data communications between and among, the devices and systems depicted in FIG. 1.

FIG. 2 is a diagram illustrating operations of, and data communications between and among, the devices and systems depicted in FIG. 1. As shown, the prehospital system 100 is depicted as including the physiologic monitor 110, the ePCR system 120, the point-of-care blood analyzer 130, and the controller/gateway 140. Starting at the left-hand side of the drawing, the physiologic monitor 110 performs a number of functions, including measurement and display of the patient's vital signs 111, defibrillation of the patient 112 (in the case where the physiologic monitor is part of a defibrillator/monitor device), and acquisition of diagnostic ECGs 113. The ePCR system 120 collects patient, diagnostic, and treatment information 121. Such information could be manually entered by the prehospital care provider, automatically documented via the local area connection to the physiologic monitor or the blood analyzer, or obtained from an existing electronic medical record for the patient, which could be retrieved from a remotely located hospital via the controller/gateway 140. The point-of-care blood analyzer 130 analyzes blood samples 131. As shown, the system is designed to communicate outputs or results of these functions with the controller/gateway 140, which receives and forwards data, as indicated by reference numeral 141, and can also control the display of results, checklists, etc. on a display built into the physiologic monitor 110, as indicated by reference numeral 142. (The point-of-care blood analyzer may be configured to communicate its output or results directly to the physiologic monitor and/or ePCR, and the latter may communicate these on to the gateway. In other words, the gateway is not necessarily required to be involved in communications amongst the components of the LAN, and may only get involved if that LAN needs to connect to a remote location. Further, the gateway need not be involved in controlling display of blood analysis results on, e.g., the physiologic monitor, or communicating information about the blood test from the analyzer to the ePCR. In other words, the controller functionality of 142 could be within the physiologic monitor, or the ePCR, instead of within the gateway. Alternatively, the controller functionality could reside within the cloud network 200.) The cloud network 200 receives data from the controller/gateway 140 and forwards data to the remote system 300, which as indicated may be located at a hospital 310. Alternatively, or in addition, This processing/analysis could be for purposes of feedback to the EMS personnel, or it could also be for purposes of integration/synthesis of multiple data elements from the prehospital system that then gets forwarded on to the remote system 300.) The remote system 300 receives and distributes data 301 and, in the case of a hospital, alerts hospital providers to the results of the blood analysis, and may also initiate a resource mobilization or care protocol in preparation to receive and treat the patient, as indicated by reference numeral 302. The remote system 300 may also provide information (feedback or other pertinent information) to the EMS personnel via the cloud network 200, as indicated by reference numeral 202.

Following are examples of such an integration of a point-of-care blood analyzer into a local area network for an emergency monitor-defibrillator and a prehospital telemedicine system.

One goal of the present disclosure is to provide early identification and awareness of a patient's elevated risk for contrast-induced nephropathy, for a patient who is attended to by an EMS provider, and who may have an emergent condition requiring, upon arrival at a hospital, expedited radiologic imaging involving a radiographic contrast agent. Examples of such patients include those experiencing an acute myocardial infarction exhibiting ST-elevation on a 12-lead ECG (STEMI), or those experiencing an acute stroke. The following explanation pertains to a STEMI patient, for whom this goal can be achieved with a monitor-defibrillator local area network incorporating components capable of:

1) measuring a 12-lead ECG of a patient exhibiting signs and symptoms suspicious for acute myocardial infarction,
2) obtaining or inputting patient vital signs and demographic information,
3) obtaining a blood test measurement of one or more indicators of the patient's kidney function, such as creatinine, and
4) integrating the above information such that it can identify for the pre-hospital care personnel, and transmit ahead to a hospital that will receive and treat the patient, information concerning both the patient's need for emergent coronary angiography as well as the patient's risk for contrast-induced nephropathy that might result from the angiography procedure.

An advantage of such a system is that it would differentiate a pre-hospital ST-Elevation Myocardial Infarction (STEMI) detection/alert system. (STEMI is a very serious type of heart attack during which one of the heart's major arteries, i.e., one of the arteries that supplies oxygen and nutrient-rich blood to the heart muscle, is blocked. ST-segment elevation is an abnormality detected on the 12-lead ECG.) This would provide the opportunity to further improve patient outcomes by early identification and hospital notification of those patients most at risk for contrast-induced nephropathy, allowing the hospital team to prepare, and take or direct actions to mitigate that risk.

STEMI alert systems have improved care and outcomes for patients experiencing ST-elevation myocardial infarction. In a typical field STEMI alert system, one or more pre-hospital 12-lead ECGs is taken, and if ECG characteristics consistent with ST-elevation criteria are observed, the ECG and/or the interpretation of the ECG is forwarded to a receiving hospital to allow activation of the cardiac catheterization lab, and other preparations designed to reduce the time from patient arrival to the catheterization procedure.

While the catheterization procedure is highly beneficial to the patient, and often life-saving, the associated angiographic imaging requires use of a radiographic contrast agent. The physiochemical properties of contrast agents can cause acute injury to the kidney that might complicate the patient's recovery, particularly in a patient with pre-existing compromised kidney function. Because there are steps that can be taken to mitigate the risk of contrast-induced nephropathy if such risk is present, kidney function is frequently assessed via blood analysis prior to angiography procedures. However, with the expedited flow of the patient to the catheterization lab that is the goal of a STEMI alert system, it is important to minimize the time required to execute the various steps of the emergency care process. Even performing a relatively rapid point-of-care blood test once the patient arrives at the hospital risks delaying the angiographic procedure and associated emergency treatment. In this situation, it would be beneficial to have advance knowledge of the patient's kidney function, in conjunction with the advance notification of the patients need for the catheterization procedure provided by the 12-lead ECG transmitted to the hospital.

Point-of-care blood testing is feasible for a variety of analytes, including markers for kidney function such as serum creatinine. Knowledge of the creatinine value, either alone or in conjunction with patient demographic info such as age, gender, weight, and race, can be used to identify patients with significantly compromised kidney function. Such patients are most at risk for contrast-induced nephropathy.

Early identification of a STEMI patient with significantly compromised kidney function could allow pre-hospital and/or hospital personnel to coordinate efforts to reduce the risk of the patient developing contrast-induced nephropathy, such as administering fluids or medications, performing remote ischemic preconditioning, or adjusting details of the planned imaging procedure. A STEMI alert system that included early identification of patient's with significantly compromised kidney function, and automated pre-arrival alerting of the hospital providers to this aspect of the patient's condition, would allow for better patient care and outcomes than a STEMI alert system without such capability.

In light of the above, the present disclosure involves a monitor/defibrillator local area network and telemedicine system, such as the telemedicine system described above, that can perform the following tasks:
1) measure a 12-lead ECG of a patient,
2) optionally obtain patient demographic information,
3) optionally obtain patient vital sign information,
4) optionally obtain patient medical history/status information,
5) measure, or obtain a measurement of, the patient's serum creatinine level, via a point-of-care blood test,
6) transmit the creatinine level, along with the 12-lead ECG or STEMI alert, and also optionally a nephropathy risk score that integrates the creatinine level with patient demographic and medical history information, to one or more remote destinations, and
7) optionally present an integrated nephropathy risk score to the pre-hospital personnel, along with guidance on treatment steps that can be taken to mitigate the patient's risk.

While point-of-care blood analysis systems exist that can measure creatinine level, those systems are not integrated with other patient diagnostic information, cannot automatically access patient demographic and medical status information existing in electronic format in other devices in the pre-hospital patient care setting, and cannot automatically transmit the integrated insight from the combination of the above to a hospital or other remote personnel.

Options and alternative embodiments include:
1) After obtaining a 12-lead indicative of STEMI, the monitor-defibrillator system can immediately transmit the 12-lead ECG or STEMI alert, in conjunction with prompting the user to perform a blood analysis to measure serum creatinine. Such measurement could be made by:
   a. a module component of the monitor-defibrillator designed to perform point-of-care blood analysis; or
   b. a separate device designed to perform point-of-care blood analysis. In this case the result of the blood test can be automatically obtained by the monitor-defibrillator from the separate device via wired or wireless communication, without any need for further user action or input beyond obtaining the blood sample to initiate the test.
   The blood test result can then be automatically integrated with other information in the monitor-defibrillator system, and/or automatically transmitted to a remote destination such as a hospital. In a preferred embodiment, this remote destination is the same hospital to which the 12-lead ECG or STEMI alert was previously transmitted.
2) In addition to measuring serum creatinine, the monitor/defibrillator also optionally can obtain patient demographic info such as age, gender, weight, and race. Such demographic info could be obtained by:
  a. prompting for entry of such information on the monitor/defibrillator system; and
  b. automatically transferring such information that may already exist in another electronic device involved in caring for the patient, such as an electronic patient care reporting tablet.
3) In addition to measuring serum creatinine, the monitor/defibrillator also optionally can obtain patient medical history/status information. Such information could be obtained by:
  a. prompting for entry of such information on the monitor/defibrillator system; and
  b. automatically transferring such information that may already exist in another electronic device involved in caring for the patient, such as an electronic patient care reporting tablet.
  c. automatically transferring such information that may already exist in a remotely stored electronic medical record.
4) The monitor/defibrillator could optionally utilize the creatinine measurement in conjunction with the patient demographic information to estimate creatinine clearance, and provide that calculation instead of or in addition to the raw creatinine value.
5) The monitor/defibrillator could optionally utilize the creatinine measurement in conjunction with both the patient demographic information and the patient medical history/status information to estimate a risk score for contrast-induced nephropathy. As one example, such a score might incorporate individual known risk factors for contrast-induced nephropathy, including renal insufficiency as indicated by an elevated creatinine level, a history of diabetes, heart failure, or anemia, advanced age, and low blood pressure.
6) The monitor/defibrillator could make available any of the above permutations of raw data or derived risk estimates in multiple modalities, including:
  a. on the screen of the monitor/defibrillator;
  b. automatically transmitted as a follow-up report to the same remote destinations to which the initial 12-lead, or STEMI alert message, were transmitted; and
  c. integrated into the 12-lead report or STEMI alert message as additional diagnostic information.

The monitor/defibrillator could additionally include protocol prompting or decision-assist functionality to guide the pre-hospital caregivers on steps to take to mitigate risk in patients with identified STEMI and elevated creatinine, including administration of fluid and/or specific medications, or application of remote ischemic preconditioning.

Considering the above detailed description of the manner in which a monitor-defibrillator local area network inclusive of a point-of-care blood analyzer and incorporating telemedicine capability could enhance care of a STEMI patient, it will be evident that various other types of critically ill patients initially encountered by EMS and requiring emergent hospital treatment can be similarly benefited by a prehospital blood analysis automatically integrated with other prehospital patient, diagnostic and care information, and automatically transmitted ahead to a hospital care team, allowing that team to more optimally prepare for the patient's arrival and expedite their emergent care. This includes, for example, other types of patients requiring emergent contrast-enhanced imaging procedures, such as patients with acute stroke, as well as patients with coagulopathy requiring mobilization of blood products, and patients on chronic anticoagulation medication requiring mobilization of anticoagulant reversal agents to treat life-threatening bleeding.

Figure 3:
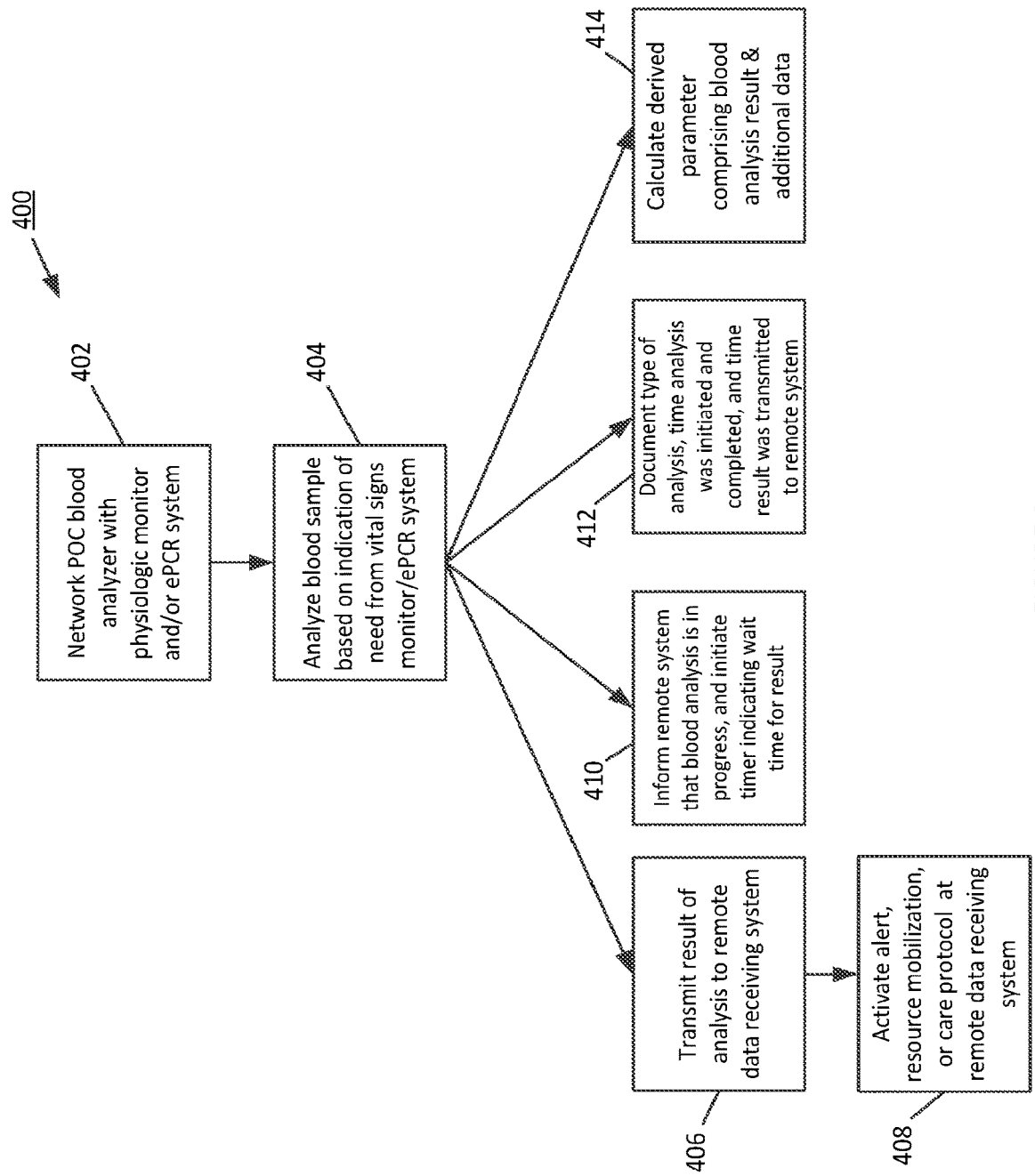
FIG. 3 is a flowchart of an inventive method of using a prehospital telemedicine system to improve treatment of a patient undergoing a medical emergency.

We will now briefly summarize our inventive method of using a prehospital telemedicine system to improve treatment of a patient undergoing a medical emergency. Referring to the flowchart of FIG. 3, an illustrative embodiment the method 400 begins with step 402, comprises networking a point-of-care blood analyzer with a physiologic monitor and/or an ePCR system. Next, at step 404, the blood analyzer is used to perform an analysis of a blood sample from the patient based on an indication of a need for a specific blood analysis provided by either the physiologic monitor and/or the ePCR system. This indication of a need for a specific blood analysis could be based on a checklist, a prompted protocol, a clinical decision rule, a combination of vital signs and patient demographic or assessment information. Alternately, the determination to perform a specific blood analysis could be at the discretion of the prehospital provider. Next, in cases where the prehospital system is communicatively connected with a hospital or other remote data receiving system, step 406 is carried out. In this step, the result of the blood analysis is automatically transmitted to the remote system (for example, the hospital). The transmission to the remote system could also include other patient data along with the result of the blood analysis (for example, the result of other diagnostic tests such as a 12-lead ECG, or details of the patients demographics, complaint, physical assessment, or vital signs). Next, at step 408, an alert, resource mobilization, or patient care protocol is activated at the remote system. For example, in cases where the remote system is located at a hospital to which the patient will be sent, hospital personnel are alerted to mobilize necessary resources and otherwise prepare to treat the patient as soon as possible after he or she arrives. Such mobilization could include activation of a catheterization laboratory, preparation and delivery of blood products from a blood bank, preparation and retrieval of a medication from a pharmacy, reservation of CT scanner availability, or other actions involved in time-critical care of critically ill patients. Steps 410, 412, and 414 are additional, optional steps that may be performed in parallel with steps 406 and 408. In step 410, the remote system is informed that the blood analysis is in progress and a timer is initiated at the remote system to indicate either the amount of time remaining until the blood analysis result will be available or the time (i.e., time of day) at which the analysis result will be available. In step 412, the prehospital system (for example, ePCR or physiologic monitor) automatically documents one or more of the type of blood analysis performed, the time the analysis was initiated was transmitted to the remote data receiving system. In step 414, a derived parameter comprising both the result of the blood analysis and the additional data extracted from ePCR system is derived. The derived parameter may represent, for example, the patient's risk for contrast-induced nephropathy. The derived parameter could alternatively be calculated based on specific patient information entered by a user of the prehospital system. Moreover, as discussed above in connection with FIGS. 1-3, additional steps and variations of the steps depicted in FIG. 3 may be carried out. FIG. 3 is intended to depict some of the primary steps that may be advantageously carried out using the inventive prehospital telemedicine system described herein.

Increased Biomarker Measurement Accuracy Through Multiplexing

Measuring the concentration of biomarkers or chemical compounds (referred to hereafter as "molecules" or "analytes") in biological samples is an important tool and source of information in clinical diagnostics and decision making. Many point-of-care assays/assay kits and readers (collectively referred to hereafter as "point-of-care labs" or "point-of-care systems") exist for measurement of various molecules, such as cardiac troponin, lactate, D-dimer, etc. Some of these labs measure a single target molecule, such as cardiac troponin. Other point-of-care labs measure multiple different target molecules in a single test, which is known as multiplexing. In this case, point-of-care labs make a single measurement for each target molecule. Utilization of the multiplexing capabilities in point-of-care labs has focused on providing measurements of more than one molecule in an attempt to widen the diagnostic capabilities/utility and reduce the time to diagnosis/treatment.

This specification describes methods by which such point-of-care labs can be used to improve the analytical accuracy for measuring the concentration of one or more molecules. Specifically, rather than having each multiplexing channel measure a different molecule, multiple channels are used to make multiple simultaneous measurements of the same molecule. Since uncertainty in measurements are largely derived from random noise in the system being measured and/or the method of measurement, multiple simultaneous measurements would allow reduction in uncertainty through statistical treatment of a greater number of measurements.

One benefit of utilizing the multiplexing capabilities of point-of-care labs is the ability to make a significant number of measurements without the additional cost of time.

The current standard in detection and measurement of various molecules, but especially biomarkers, are limited to central labs in hospitals or laboratory contractors. The equipment is costly, the personnel are highly trained, and the results often take extensive time and money to obtain. In recent years, point-of-care testing has become a popular topic where the attempt is to perform detection of various molecules, including biomarkers, at the patient's bedside where the results would be rapidly available to the clinician for decision making and cost a fraction of the central labs.

Recently, some point-of-care systems have been developed with multiplexing capabilities and as such, have made possible the simultaneous measurement of multiple molecules from a single sample in a single test. So far, the multiplexing capability has been focused on the measurement of multiple molecules and developing panels of tests meant to aid in the detection of specific conditions, such as sepsis. By using this approach it is hoped that a wider range of molecules can be measured in a shorter amount of time leading to a larger amount of data for rapid, emergency clinical decision making.

Existing point-of-care systems, however, lack the accuracy to match the performance of the central labs. Furthermore, for the measurement of molecules in some conditions, accuracy and sensitivity (analytical) may be desired over a larger panel of molecular measurements. For example, in the detection of MI an MI panel for the point-of-care system may include CKMB, myoglobin, and cardiac troponin (cTn). (There are 3 isoenzymes of creatine kinase (CK)-BB, -MM, and -MB. The primary source of CKMB is myocardium, although it is also found in skeletal muscle. CKMB levels increase with myocardial damage.) Yet the scientific consensus is that CKMB and myoglobin do not add value to the diagnosis of MI if cTn measurement is available. In fact, extensive but ongoing work suggests that increased accuracy of cTn measurements can add significant value to the appropriate diagnosis of MI. Nevertheless many point-of-care systems lack the analytical accuracy and sensitivity necessary to reliably detect cTn changes indicative of MI. Therefore, a method for improving the accuracy and sensitivity of the point-of-care system is needed.

This present specification proposes a method for improving point-of-care system accuracy and/or sensitivity through a novel use of the multiplexing capability to reduce uncertainty. Broadly speaking the noise leading to inaccuracy and lower sensitivity derive from two main sources: the noise produced by the system being measured and the noise produced by the measurement techniques. Both types of noise tend to be random and as such acquisition of multiple measurements followed by appropriate statistical treatment can significantly reduce uncertainty. While this does not remove systematic bias (such as sample dilution) in the results it can potentially serve to greatly reduce the uncertainty. In addition, strategies could be employed to detect systematic bias in the sample measurements. For example, sample dilution could contaminate the results for all tests from a single sample. In such cases strategies could be used to detect potential bias (described elsewhere in this document). The embodiments below describe approaches to accomplish these two goals of 1) reducing uncertainty due to random noise and 2) detect systematic bias.

In one embodiment the multiplexing point-of-care system is configured to measure the same molecule on all available channels. The measurements are obtained by the reader device and statistically treated to obtain a value and confidence level. For example, if the measurements are distributed normally a mean and standard error could be reported to the user by the device. This system would give the user not only a measured value but an estimate of confidence in the measured value.

In another embodiment, one or more channels are reserved for measurement of a "standard" molecule. A standard molecule is a molecule that is known to have an acceptably constant concentration in the biological sample taken for the condition for which the selected assay is indicated. For example, given a suspected MI patient serum albumin concentration could be measured in one or more multiplexed channels while the remaining channels measure the molecule of interest, say cTn. Assuming the concentration of albumin is consistent in most patients experiencing an MI, the detection of an abnormally low concentration of albumin could be used to detect sample dilution prior to testing thus returning either a warning or an error to the user indicating that the cTn measurement may have been diluted.

In another embodiment one or more channels could intentionally dilute the incoming sample thereby allowing measurement of molecules with higher than expected concentrations which may be outside the measurement bandwidth for the original sample. This dilution technique could be applied to either the molecule of interest or the standard molecule.

In another embodiment the chemical makeup of the reagent could be changed (pH, osmolarity, osmolality, etc.) in one or more channels. Even the solvent could be modified or varied. As an example different solvents could more effectively denature a target protein and expose an antibody binding site. By varying the solvent used in some of the multiplexed tests more than one binding site could be targeted during the same set of multiplexed tests thereby improving the confidence in the test result since the test result could be confirmed by multiple antibodies. Furthermore, each additional channel with altered makeup could be different from the previous. For example, the pH could be altered in some channels at various levels. If the effect of changing pH on the target or standard molecule binding or reaction coefficient is known, the change in measured concentrations at various pH levels could indicate that for example the blood sample was exposed to air prior to testing suggesting mishandling of the sample. In addition, this type of approach could be useful for scientific studies investigating the role of solution on protein-protein interactions as well where large amounts of data could be generated quickly and in-the-lab.

The "standard" molecule discussed in the embodiments above may be the same molecule across all assays or be a specific molecule dependent upon the suspected condition of the patient. For example, for MI the standard may be creatinine but for sepsis it might be albumin. Thus, the standard molecule does not necessarily need to be a global standard for all assays.

In another embodiment, the number of molecules of interest need not be a single molecule but multiple molecules. For example, two molecules may be of interest for a given condition, in which case the multiplexed channels may be divided equally between the two molecules or the molecule for which the assay has less sensitivity may be measured by a greater number of channels. This would allow molecules for which the chosen assay has greater sensitivity to use fewer than the molecule for which the assay has less sensitivity. Alternatively, channels could be allocated to molecules based on importance in diagnostic process.

In any of the above embodiments, whenever there is greater than one measurement of a single molecule proper statistical treatment is performed by the reader device or devices connected to the point-of-care system and the results including measured value and confidence level are conveyed to the user.

Multiplexing Strategies in a Point-of-Care Blood Testing Platform

Point-of-care systems have been developed that can multiplex assays (point-of-care multiplex systems), allowing simultaneous measurement of several different analytes (typically proteins) from a single blood sample. To date, such multiplex assays have been used to provide test results to a user who has an explicit interest in diagnosing, dispositioning, and/or risk stratifying a patient and even for mobilizing appropriate healthcare response resources for treatment of a patient based on the test results for each analyte targeted by each individual channel of the multiplexed assay. The multiplexing capability can also be used for alternative purposes, such as to increase the analytic precision of a single analyte test result presented to the user (described elsewhere in this document).

Additional novel schemes for using the analytic bandwidth of a point-of-care multiplex system include in no particular order:

Different channels of the point-of care multiplex system targeting different epitopes of the analyte or labeled analyte. The results from the additional channels can then be used, for example, to better identify interference conditions or other issues that can affect the accuracy of the test result from the primary channel. In one embodiment, the test result output to the user can be the analyte level detected via the channel or channels measuring the analyte of primary interest, along with a text or graphic indicator of the possibility or probability that the primary channel result is confounded by factors identified by the results from the additional channels.

A variation on the theme above is to target the same epitope but utilize different antibodies. It is well known that antibodies from different vendors, sources, or batches can be significantly different. Therefore, utilizing multiple high quality antibodies from different sources can reduce the likelihood of erroneous readings from a faulty batch of antibodies or give greater confidence in the level of elevated analyte by confirmation through multiple tests. In this case, the results of the most trusted antibody can be displayed to the user while disagreement on measured analyte concentration from other antibodies can be used to provide the user with an indication that a potential faulty reading was detected.

Another variation on the theme above is to target different isoforms of an analyte or even functionally related analytes with the multiplex channels. For example, for a cardiac troponin assay, use one or more channels to test for Troponin I, and one or more channels to test for Troponin T. In addition to the above-described benefit of alerting to potential interferences or other analysis confounders, this method can be used to provide insight into the nature and/or temporal evolution of troponin release. Troponin T has a larger cytosolic fraction than Troponin I, so the ratio of the two levels can, for example, provide insight into the balance between reversible injury vs. necrosis of myocytes, or for example provide insight into the elapsed time since the onset of ischemic effects on myocyte membrane and structural integrity. In this scheme, the test result output to the user can for example be the analyte level detected by the primary channel (e.g. Troponin I), along with text or graphic indicators representing the estimated temporal location within the acute ischemic process.

Additional channels of the point-of-care multiplex system can be used to test for biomarkers with specificity for alternative pathology vs. the primary pathology being evaluated with the primary assay channel, where such alternative pathology can create or contribute to a "false positive" elevation in the primary assay. For example, a cardiac troponin test being used in the diagnostic workup for potential AMI (acute myocardial infarction) can use additional point-of care multiplex system channels to assess levels of creatinine, lactate, etc. that can indicate non-AMI causes of elevated troponin.

As a variation on the above, the additional channels can be used to test for presence or concentrations of substances in the sample that can indicate (or rule out) a suboptimal or contaminated sample caused for example by a poor sampling technique. For example, a normal albumin concentration can reduce concerns that the blood sample may be diluted with a significant amount of saline or other intravenous (IV) fluid. An elevated free hemoglobin level can indicate that hemolysis is a concern with a given blood sample. Combinations of tests utilizing the additional channels can provide increased specificity for certain suboptimal sample issues even in the setting of potential disease that can explain an abnormal value of any individual additional-channel test. For example, an elevation of both free hemoglobin and potassium may be more likely to indicate hemolysis due to improper blood sample procurement/handling vs. due to disease, when compared to assessment of just free hemoglobin or potassium alone. Likewise, while creatinine, albumin, and (RBC) hemoglobin concentrations can all become abnormally low with certain disease states, if all 3 are simultaneously low, especially if by a similar factor, it becomes significantly more likely that the cause is dilution of the blood sample with exogenous fluid, and that therefore the result from the primary assay is likely to also be artificially low.

The multiplexing capability can be used to test several discrete blood samples for the same analyte(s). For example, samples taken from different vascular access sites, obtained via different methods (e.g. venous sample vs. finger stick), or from arterial vs. venous circulation. This can be useful in situations where local concentrations of the targeted analyte can vary (e.g. protein aggregation, coagulation activity, etc.), or when a difference in results obtained via different sampling methods can help either provide a baseline calibration for ongoing use of the less invasive/complex method, or help identify circumstances where there is confounding of the test result.

A key characteristic of all of the above schemes is that the results from the additional channels are not provided as raw information to the user; rather they are interpreted by preconfigured criteria or algorithms within the testing device (and/or any connected element of a medical monitoring/information system). In the preferred embodiment, only summarized context information is provided to the user in conjunction with the quantitative result of the primary channel or channels if the primary test is performed multiple times. Examples of such summarized context information include messages/alerts/graphics indicating: "result may be affected by interferences in the sample", "result may be affected by alternate (e.g. non-cardiac) pathology", etc.

In another embodiment, the results from the additional channels influence what is done with the result data from the primary assay channel. For example, the context results from the additional channels can:
- inhibit display and/or transmission of the result from the primary channel,
- recommend re-running the primary assay with a new blood sample,
- display quantitative or qualitative results from the additional channels only when they meet certain thresholds or patterns that have significance with respect to the interpretation of the primary assay result,
- display and/or transmit a warning that the user can override if desired To accomplish any of the above-described schemes, two or more consecutive multiplexed assays can be run on one or more point-of-care multiplex system in order to provide enough additional channels of multiplexing bandwidth to obtain the necessary results. In such a scheme, the testing platform can provide a preliminary test result for the primary analyte after the first assay is run, and then update that initial result with the additional context and interpretive guidance provided by the results of the second assay, including data from additional devices. In any of the above schemes, multiple channels can be used to replicate the same primary assay and/or additional tests to improve the precision of those results.

CONCLUSION

The true scope the present invention is not limited to the illustrative or exemplary embodiments disclosed herein. As will be understood by those skilled in the art, many of the inventive features described herein are implemented with software running on a special purpose hardware platform. Moreover, other embodiments within the scope of protection of the following claims include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

We claim:

1. A prehospital telemedicine system, comprising:
a gateway device in a local area network, the gateway device configured to communicate with a remote data receiving system of a medical facility over a cellular link;
a point-of-care (POC) blood analyzer communicatively connected in the local area network to the gateway device, wherein the POC blood analyzer is configured to begin analysis of a blood sample of a patient before the patient arrives at the medical facility and provide a result of the analysis of the blood sample to the gateway device; and
an electronic patient care reporting (ePCR) system communicatively connected in the local area network to the gateway device, wherein the ePCR system is configured to collect patient information of the patient and provide the patient information to the gateway device, wherein the ePCR system is configured to restrict use of the POC blood analyzer prior to completion of an electronic checklist and taking a combination of vital signs, wherein completion of the electronic checklist and the taking of the combination of vital sign triggers the ePCR to provide an electronic signal to the POC blood analyzer that enables the point-of-care blood analyzer to perform the analysis, and
wherein the gateway device is configured to transmit the result of the analysis of the blood sample and the patient information to the remote data receiving system of the medical facility.

2. The prehospital telemedicine system of claim 1, wherein the patient information comprises patient demographic information, and wherein the gateway device is configured to transmit the patient demographic information together with the result of the analysis of the blood sample.

3. The prehospital telemedicine system of claim 2, wherein the patient demographic information is entered by a prehospital care provider using the ePCR system.

4. The prehospital telemedicine system of claim 3, wherein the ePCR system is configured to prompt the prehospital care provider to enter the patient demographic information.

5. The prehospital telemedicine system of claim 2, wherein the ePCR system is configured to obtain the patient demographic information from an electronic record.

6. The prehospital telemedicine system of claim 5, wherein the electronic record is an electronic medical record.

7. The prehospital telemedicine system of claim 1, wherein prehospital telemedicine system is further configured to: combine the result of the analysis of the blood sample with the patient information; and transmit information derived from a combination of the result of the analysis of the blood sample with the patient information to the remote data receiving system of the medical facility.

8. The prehospital telemedicine system of claim 7, wherein the patient information comprises a complaint, and wherein the combination of the result of the analysis and the patient information comprises the complaint.

9. The prehospital telemedicine system of claim 7, wherein the patient information comprises a physical assessment, and wherein the combination of the result of the analysis and the patient information comprises the physical assessment.

10. The prehospital telemedicine system of claim 1, further comprising a physiologic monitor, wherein the local area network is a local area network of the physiologic monitor.

11. The prehospital telemedicine system of claim 10, wherein the gateway device is a component of the physiologic monitor.

12. The prehospital telemedicine system of claim 1, wherein the gateway device is a component of the ePCR system.

13. The prehospital telemedicine system of claim 1, wherein the POC blood analyzer is configured to measure creatine kinase-MB (CK-MB), myoglobin, cardiac troponin (cTn), lactate, or D-dimer.

14. The prehospital telemedicine system of claim 1, wherein the ePCR system is further configured to: determine, based at least on the patient information, that it is appropriate to analyze the blood sample; and cause display of a prompt indicating that it is appropriate to analyze the blood sample.

15. The prehospital telemedicine system of claim 1, further comprising a physiologic monitor configured to obtain physiologic data, wherein the gateway device is configured to transmit the physiologic data with the result of the analysis of the blood sample to the remote data receiving system of the medical facility.

16. A method comprising:
analyzing a blood sample of a patient using a point-of-care (POC) blood analyzer of a prehospital telemedicine system before the patient arrives at a medical facility;
providing, by the POC blood analyzer, a result of the analyzing of the blood sample to a gateway device in a local area network, wherein the gateway device is configured to communicate with a remote data receiving system of the medical facility over a cellular link;
collecting patient information of the patient using an electronic patient care reporting (ePCR) system communicatively connected in the local area network to the gateway device, wherein the POC blood analyzer is restricted from analyzing the blood sample prior to completion of an electronic checklist and taking a combination of vital signs, and wherein completion of the electronic checklist and the taking of the combination of vital sign triggers the ePCR to provide an electronic signal to the POC blood analyzer that enables the point-of-care blood analyzer to analyze the blood sample;
providing, by the ePCR system, the patient information to the gateway device; and
transmitting, by the gateway device, the result of the analysis of the blood sample and the patient information to the remote data receiving system of the medical facility.

17. The method of claim 16, wherein the prehospital telemedicine system is carried in an emergency services vehicle.

18. A local area network of a prehospital telemedicine system, the local area network comprising:
a gateway device configured to communicate with a remote data receiving system of a medical facility over a cellular link;
a point-of-care (POC) blood analyzer configured to begin analysis of a blood sample of a patient before the patient arrives at the medical facility and provide a result of the analysis of the blood sample to the gateway device, wherein the POC blood analyzer is restricted from analyzing the blood sample prior to completion of an electronic checklist and taking a combination of vital signs; and
an electronic patient care reporting (ePCR) system configured to collect patient information of the patient and provide the patient information to the gateway device, wherein completion of the electronic checklist and the taking of the combination of vital sign triggers the ePCR to provide an electronic signal to the POC blood analyzer that enables the point-of-care blood analyzer to analyze the blood sample,
wherein the gateway device is configured to transmit the result of the analysis of the blood sample and the patient information to the remote data receiving system of the medical facility.

19. The local area network of claim 18, wherein the gateway device is configured to transmit an indication that the analysis of the blood sample is in progress or the result of the analysis of the blood sample to the remote data receiving system before the patient arrives at the medical facility.

* * * * *